United States Patent [19]

Laine

[11] 4,226,845
[45] Oct. 7, 1980

[54] WATER GAS SHIFT REACTION AND IN THE HYDROFORMYLATION AND HYDROHYDROXYFORMYLATION REACTIONS

[75] Inventor: Richard M. Laine, Mountain View, Calif.

[73] Assignee: S R I International, Menlo Park, Calif.

[21] Appl. No.: 967,028

[22] Filed: Dec. 6, 1978

[51] Int. Cl.$^3$ .......................... C01B 1/02; C01B 2/06; C07C 45/08; C07C 29/16
[52] U.S. Cl. .................................... 423/655; 252/373; 252/443; 568/451; 568/882
[58] Field of Search ................ 423/655, 656; 252/373, 252/443; 260/449 R, 449 L, 604 HF; 568/882

[56] References Cited

U.S. PATENT DOCUMENTS

| | | | |
|---|---|---|---|
| 3,020,314 | 2/1962 | Alderson | 260/597 |
| 3,239,566 | 3/1966 | Slaugh et al. | 260/604 HF |
| 3,490,872 | 1/1970 | Fenton | 423/656 |
| 3,786,132 | 1/1974 | Dawes | 423/117 |
| 3,984,478 | 10/1976 | Homeier | 260/604 HF |
| 4,107,076 | 8/1978 | Einsenberg et al. | 423/656 X |
| 4,144,191 | 3/1979 | Hartwell et al. | 252/428 |

FOREIGN PATENT DOCUMENTS 638754 6/1950 United Kingdom.

OTHER PUBLICATIONS

JACS., 99 8323-8325, Dec. 7, 1977.
Chemical Week, Apr. 19, 1978, pp. 63 & 65.
Chemical & Engineering News, Apr. 3, 1978, pp. 26 & 27.
JACS., 100 4595-4597, Jul. 5, 1978.
JACS., 100 6451-6454, Sep. 27, 1978.
JACS., 100 6527-6528, Sep. 27, 1978.
Igbal, Helvetica Chimica Acta, 54, 1440-1445 (1974).
Laine "J. Am. Chem. Soc.", 99, Jan. 1977, pp. 252-253.

Primary Examiner—Edward J. Meros
Attorney, Agent, or Firm—Edward B. Gregg; Donovan J. DeWitt

[57] ABSTRACT

In the water gas shift reaction, $$H_2O + CO \rightarrow H_2 + CO_2$$

and more particularly in hydroformylation of olefins, e.g. ethylene $$CH_2=CH_2 \xrightarrow[\text{or } 2CO + H_2O]{CO + H_2} CH_3-CH_2-CHO$$

and in hydrohydroxymethylation in which an alcohol, e.g. propanol, is produced, higher yields and/or fewer by-products and branched chain products and/or faster reactions are obtained using a combination of two or more Group VIII metal carbonyls one of which is ruthenium.

8 Claims, No Drawings

WATER GAS SHIFT REACTION AND IN THE HYDROFORMYLATION AND HYDROHYDROXYFORMYLATION REACTIONS

The Government has rights in this invention pursuant to Grant No. 77-21246 and IPA No. 0016 awarded by the National Science Foundation.

The invention relates to the improvement in the water gas shift reaction (WGSR) and, more particularly, in the hydroformylation and hydrohydroxymethylation reactions.

The water gas shift reaction is as follows:

$$H_2O + CO \rightarrow H_2 + CO_2 \quad (1)$$

The hydroformylation reaction is as follows:

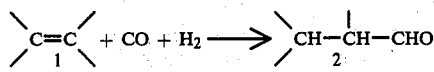

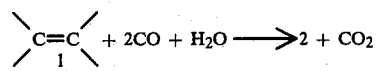

wherein the group $>C=C<$ is a cyclic or acyclic olefin group

The hydrohydroxymethylation reaction results in the production of an alcohol which may be regarded as the reduction product of aldehyde 2

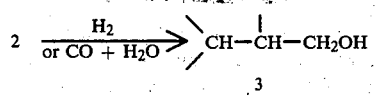

However, it is not certain whether the aldehyde 2 produced in reaction (2) or (2a) is reduced to the alcohol 3, or whether an intermediate is formed which in turn produces the aldehyde 2 and the alcohol 3 in varying proportions. At present I regard reaction (3) as more likely. In any event, it is known that the catalyzed reaction of an olefin 1 with CO and $H_2$ (or $H_2O$) results in a mixture of 2 and 3.

It is desirable to conduct WGSR and hydroformylation/hydrohydroxymethylation reactions in a solution of a catalyst rather than using a heterogenous catalyst. Further, it is desirable that the amount of by-products, such as branched chain aldehydes and alcohols, and aldol condensation of the aldehyde 2 be minimized and that the yield of the desired aldehyde or aldehyde plus alcohol be high, etc. (Hereinafter the term "formylation" is used to refer to both hydroformylation and hydrohydroxymethylation.)

It is an object of the present invention to provide improvements in these reactions, such as a high yield of the desired end product, selectivity (i.e., production of straight chain products rather than branched chain products), etc.

If the olefin 1 is a branched chain alkene, the product will accordingly be branched. Therefore what is means by "selectivity" is that the olefinic group $>C=C<$ be converted in high yield to the aldehyde 2 and/or the alcohol 3.

The above and other objects of the invention will be apparent from the ensuing description and appended claims.

It is known to use Group VIII metal carbonyls as catalysts for the WGSR, e.g. ruthenium carbonyls. See Laine, Rinker and Ford, J.A.C.S. 99, 252, 253, January 1977. Also in a paper by Iqbal in Helvetica Chemica Acta, 54, 1440–1445 (1971) the aminomethylation of olefins by reaction with CO, $H_2O$ and a secondary amine using rhodium oxide and/or iron pentacarbonyl is described. The rhodium oxide forms a rhodium carbonyl in situ. See also Fenton U.S. Pat. Nos. 3,539,298 and 3,490,872.

I have found that in the WGSR reaction, and more particularly in the formylation reactions, improved yields and/or improved selectivity and/or faster reaction rates result from certain conditions as follows:

(1) The employment of a mixture of two or more Group VIII metal carbonyls one of which is ruthenium.

(2) The employment of an alkaline pH by reason of the use of potassium hydroxide, carbonate or bicarbonate or mixtures thereof. Cesium or rubidium may be substituted for potassium.

In the hydroformylation reaction (and the concomitant hydrohydroxymethylation reaction) potassium (or Cs or Rb) alkoxides and phenolates may be used in the absence of water.

Other aspects of the invention will appear hereinafter. At present the conjoint use of an Ru/X carbonyl and KOH, $K_2CO_3$ or $KHCO_3$ will be described, X being any other Group VIII metal, i.e., any one or more of Fe, Co, Ni, Rh, Pd, Os, Ir or Pt. Taking the case of a pair of Group VIII metals one of which is Ru and the other a Group VIII metal X, the proportion of Ru and X (on an atomic basis) may range from 1% to 99% of Ru and 99% to 1% of X. Preferably the range is 10% to 90% of Ru to 90% to 10% of X, most advantageously 25–75% Ru to 75–25% X.

The reaction may be carried out at temperatures of 100° to 350° C., at pressures of 1 atmosphere to 1000 atmospheres of CO or CO+$H_2$ along with other gases. The reaction as described in the examples below is carried out in batch fashion in a bomb but continuous procedures may be employed.

In the formylation reaction the olefin may be any of the C-2 to C-25 olefins. Mixtures may be used when a mixture of aldehydes or alcohols is desired.

The catalyst may be employed in amounts of 0.01 mole to 1.0 mole percent based upon the added olefin.

In reaction (2a), where water is used, it may be present in the amount of 1.0 to 20 moles per mole of olefin.

Table I sets forth results in the catalysis of the WGSR comparing the relative activities of Ru, Fe and Ru/Fe catalyst complexes.

TABLE I

| Catalyst Complex | Activity (±5) |
|---|---|
| $H_4Ru_4(CO)_{12}$ | 60 |
| $Ru_3(CO)_{12}$ | 50 |
| $Fe(CO)_5$ | 40 |
| 1:1 molar ratio of $Fe_3(CO)_{12}$ and $Ru_3(CO)_{12}$ | 70 |

The reaction was carried out in a bomb. Temperature was 135° C.; pressure of CO was 54 atmospheres; reaction was carried out in a sealed quartz-lined vessel, with magnetic stirring; solvent was 6 ml methanol containing 0.055 mol $H_2O$ and 3 mmol KOH; activity was moles $H_2$ per mol of catalyst per day as determined by calibrated, temperature-programmed GC analysis.

Table II sets forth activities of various Ru, Fe and Ru/Fe catalysts for catalysis of the WGSR under different conditions.

TABLE II

| Catalyst Complex[a] | Reaction Medium | Activity[b] |
|---|---|---|
| $Ru_3(CO)_{12}$ | KOH/ethoxyethanol[c] | 2.8(0.9) |
| $Fe(CO)_5$ | KOH/ethoxyethanol[c] | 1.0)1.0) |
| $Ru_3(CO)_{12}/Fe(CO)_5$[d] | KOH/ethoxyethanol[c] | 7.4(4.2) |

[a]Except where noted, 0.04 mmol of each complex listed was added to the solution.
[b]Moles of $H_2$ per day per mole of complex [moles of $Ru_3(CO)_{12}$ plus moles of $Fe(CO)_5$]. Value in parentheses are normalized activities: moles of $H_2$ per day per gram-atom of metal added initially to the system.
[c]2 mmol of KOH, 0.02 mol of $H_2O$, 3.0 ml of ethoxyehtanol.
[d]0.04 mmol of $Ru_3(CO)_{12}$/0.064 mmol of $Fe(CO)_5$.

Table III sets forth data concerning the formylation of 1-pentene with CO and $H_2O$. The conversion figures in the second column are percent conversions to combined aldehyde $C_6H_{12}O$ and alcohols $C_6H_{14}O$; the figures in Columns 3 and 4 not in parentheses are millimoles; the figures in parentheses are percentages of the aldehyde (Column 3) and alcohol (Column 4) which have straight chains.

TABLE III

| Reactor: | Parr General Purpose Bomb reactor quartz or teflon lined 35 ml volume. |
|---|---|
| Catalyst Solution: | 6.0 ml MeOH, 1.0 ml 3.0 N KOH, 36 mmoles 1-pentene 800 psi CO, 150° C. |
| Reaction Time: | 0.5 hr for all reactions. |

| | Product Yield Based on Available CO | | |
|---|---|---|---|
| Catalyst Complex* | Combined (aldehyde + alcohol Conversion | Conversion to Aldehyde | Conversion to Alcohol |
| (1) $Fe_3(CO)_{12}$ | 22% | 5.10 (85%) | 0.62 (91%) |
| (2) $Ru_3(CO)_{12}$ | 26% | 6.60 (97%) | 0.10 (97%) |
| (3) 25% (1), 75% (2) | 42% | 10.80 (92%) | 0.20 (9.5%) |
| (4) 50% (1) 50% (2) | 52% | 13.00 (92%) | 0.60 (95%) |
| (5) 75% (1) 25% (2) | 54% | 12.50 (92%) | 1.50 (95%) |

*Where mixtures were used [entries (3), (4) and (5)] the sum total of catalyst complex was 0.1 mmol, percentages are molar ratios.

Other aspects of the invention include the following: The hydrohydroxymethylation reaction may be used to reduce aldehydes to alcohols where the aldehyde is suitable as the starting material rather than an olefin. The formylation reaction may be applied to cyclic (included ring substituted cyclic), acyclic (including straight and branch chain/acyclic and mixed (cyclic-acyclic) olefins; also to the conversion of alkenyl substituted aromatic compounds.

Pairs of Group VIII metals Ru/X that I have investigated and have found to be improvements upon Ru or X alone are the following:

$Ru_3(CO)_{12}/Fe_3(CO)_{12}$
$Ru_3(CO)_{12}/Os_3(CO)_{12}$
$Ru_3(CO)_{12}/Rh_6(CO)_{16}$
$Ru_3(CO)_{12}/Co_2(CO)_8$
$Ru_3(CO)_{12}/Ir_4(CO)_8$

I have also obtained good results with a pair that does not include ruthenium, namely $(Rh)_6(CO)_{16}/Co_2(CO)_8$. The metals introduced in the form of oxides or salts may be in any valence state because they are all reduced by the system to metal carbonyl complexes which are the active catalysts. Suitable non-carbonyl source materials are chlorides, nitrates, acetates, β-diketonates, the anion being chosen so as not to be destructive of the solvent, the catalyst, the reactants and the reaction products; also oxides and phosphine derivatives such as $[(C_6H_5)_3P]_3RuCl_2$ may be used.

I claim:

1. In the production of hydrogen and carbon dioxide by the water gas shift reaction, and in the hydroformylation and hydrohydroxymethylation of olefins by reaction of the olefins with carbon monoxide and hydrogen or water and wherein a homogeneous catalyst in the form of a solution of a catalyst in a solvent is used, the improvement which comprises employing a mixed ruthenium carbonyl/iron carbonyl as a catalyst.

2. The improvement of claim 1 wherein a base is employed to render the solvent alkaline and the base is a K, Cs or Rb hydroxide, carbonate or bicarbonate.

3. The improvement of claim 1 wherein the reaction is hydroformylation/hydrohydroxymethylation and the solvent is made alkaline by K, Cs or Rb hydroxide, carbonate or bicarbonate when water and carbon monoxide are reactants and by K, Cs or Rb hydroxide, carbonate, bicarbonate, alkoxide or phenolate when hydrogen and carbon monoxide are reactants and water is excluded.

4. In the hydroformylation/hydrohydroxymethylation of olefins by reaction of an olefin with carbon monoxide and either hydrogen or water, the improvement which comprises using as the reaction medium/catalyst a solution of a ruthenium carbonyl and an iron carbonyl, said solution having as the solvent a polar liquid containing a potassium cesium or rubidium base to make the reaction medium alkaline, the solvent and potassium base being selected to be compatible with the reactants, the catalyst and the reaction products.

5. The improvement of claim 4 wherein carbon monoxide and hydrogen are reacted with the olefin.

6. The improvement of claim 4 wherein carbon monoxide and water are reacted with the olefin and the base is K, Cs or Rb hydroxide, carbonate or bicarbonate or a mixture thereof.

7. In the hydroformylation and/or the hydrohydroxymethylation of an olefin by reaction of the olefin with carbon monoxide and water or hydrogen in a solution of a catalyst, the improvement which comprises providing the catalyst in the form of a mixed ruthenium carbonyl/iron carbonyl.

8. The improvement of claim 7 wherein the ruthenium carbonyl is $Ru_3(CO)_{12}$ and the iron carbonyl is $Fe_3(CO)_{12}$.

* * * * *